(12) United States Patent
Awamura et al.

(10) Patent No.: US 6,906,043 B2
(45) Date of Patent: Jun. 14, 2005

(54) RAPIDLY SOLUBLE FILM PREPARATION

(75) Inventors: Tsutomu Awamura, Toyama (JP); Kazuyoshi Furusawa, Toyama (JP); Yoshihiro Sawai, Toyama (JP)

(73) Assignee: Kyuku Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/529,234

(22) PCT Filed: Oct. 6, 1998

(86) PCT No.: PCT/JP98/04499

§ 371 (c)(1),
(2), (4) Date: Apr. 6, 2000

(87) PCT Pub. No.: WO99/17753

PCT Pub. Date: Apr. 15, 1999

(65) Prior Publication Data

US 2003/0099690 A1 May 29, 2003

(30) Foreign Application Priority Data

Oct. 8, 1997 (JP) .............................. 9-275967

(51) Int. Cl.[7] .................. A61K 31/715; A23G 3/00; A23L 1/05
(52) U.S. Cl. ..................... 514/54; 514/57; 514/60; 426/658; 426/661
(58) Field of Search .................. 514/54, 57, 60; 426/658, 661

(56) References Cited

U.S. PATENT DOCUMENTS

| | | | | |
|---|---|---|---|---|
| 4,136,162 A | * | 1/1979 | Fuchs et al. | 264/164 |
| 4,777,046 A | * | 10/1988 | Iwakura et al. | |
| 5,102,950 A | * | 4/1992 | Terada et al. | 525/60 |
| 5,656,286 A | * | 8/1997 | Miranda et al. | |
| 5,800,832 A | * | 9/1998 | Tapolsky et al. | 424/449 |
| 5,914,118 A | * | 6/1999 | Yamamura et al. | 424/402 |
| 6,042,844 A | * | 3/2000 | Ishida et al. | 424/443 |
| 6,106,856 A | * | 8/2000 | Squillante et al. | 424/448 |
| 6,294,202 B1 | * | 9/2001 | Burns et al. | 424/488 |

FOREIGN PATENT DOCUMENTS

WO    WO 87/02241    4/1987

OTHER PUBLICATIONS

Oyanagui et al, " Inhibition by Nilvadipine of Ischemic and Carrageenan Paw Edema as well as of Superoxide Radical Production from Neutrophils and Xanthine Oxidase", Arzneim.–Forsch., vol. 41, No. 5, pp. 469–474 (1991).*

* cited by examiner

Primary Examiner—James O. Wilson
Assistant Examiner—Everett White
(74) Attorney, Agent, or Firm—Edwards & Angell, LLP; David C. Conlin, Esq.; Gregory B. Butler, Esq.

(57) ABSTRACT

Disclosed is a rapidly soluble film preparation mainly comprising a drug, an edible polymer and a saccharide, a manufacturing method of which is simple, and having high elution rate.

1 Claim, 1 Drawing Sheet

RAPIDLY SOLUBLE FILM PREPARATION

TECHNICAL FIELD

The present invention relates to a film preparation (film-shaped drug) rapidly soluble in the oral cavity, and more particularly to a rapidly soluble film preparation for oral administration containing a saccharide in a base, for the purpose of allowing a drug to be mainly absorbed into the digestive organs by rapidly dissolving the drug in the oral cavity.

BACKGROUND ART

At present, as the drugs orally administered, naked tablets, coated tablets, capsules, powders, granules, pills and aqueous drugs (solutions) have been put on the market. Then, the preparations for oral application include buccal tablets and mucosa-adhesive film preparations. However, these are ones in which the drugs are allowed to be absorbed through the mucous membranes in the oral cavity, or ones for the purpose of treatment of diseases in the oral cavity, and are not ones for the purpose of usual drug absorption into the digestive tracts. Almost all of these are contrived to continuously release the drugs, and no rapidly soluble ones have been known.

Drugs commercially available as merely film-shaped, tape-shaped or sheet-shaped ones, not adhesive to the mucous membranes in the oral cavity, are not found. However, as seen from documents (patents), (A) a sheet-shaped administration formation such as medicine, confectionery, other food, a cosmetic or an article similar thereto orally administered or incorporated, which comprises 20 to 60% by weight of at least one film forming agent, 2 to 40% by weight of at least one gel forming agent, 0.1 to 35% by weight of at least one active substance (drug) and further less than 40% by weight of at least one inactive filler, and rapidly decomposes in water (Toku-Kai-Hei (Japanese Unexamined Patent Publication) 7-100186), and (B) a tape having a tensile strength of at least 200 psi (about 14 $kg/cm^2$), a $drug/mm^3$ of 0.01 to 2 mg and an optimum solubility to the drug, and having a composition comprising about 10 to 40% by weight of a physiologically acceptable thermoplastic polymer, about 15 to 50% by weight of a saccharide, about 5 to 40% by weight of a physiologically acceptable plasticizer and about 0 to 20% by weight of a physiologically acceptable lubricant (Toku-Kai-Hei 5-220203) are known. Further, (C) a sheet-shaped solid pharmaceutical composition characterized in that a solution or a suspension containing a substance having physiologically active action by the existence thereof in slight amounts is printed on, spread on, sprayed on, or injected into a pharmaceutically acceptable sheet-shaped carrier (Toku-Kai-Hei 5-124954) is also known.

However, in the above-mentioned invention (A), it is described that "it is an object of this invention to provide an administration formation rapidly decomposing in water and individually formulated in a sheet form" (the publication, page 8, right column, [0028]), but what contrivance causes the formation to rapidly decompose is not described at all. Although a drug is obtained in Example 2, merely "the drug decomposes in the mouth" (the publication, page 10, left column, [0064]) is only described, and details such as for the time for decomposition of the drug decomposes are not clear. In this Example 2, the temperature is elevated to 80° C. in preparation, so that a considerable period of time is taken for cooling after mixing and the like, which causes a disadvantage in the manufacturing process. Further, in the above-mentioned invention (B), sorbitol (lubricant) is used as one useful to enhance speeds of disintegration and dissolution of the tape. However, it is described that "for further assisting dissolution, a disintegrating agent, for example, cross caramelose Na type A, can be used in an amount of not exceeding about 10% by weight", and this is considered because the use of only sorbitol sometimes results in an insufficient disintegration rate. Furthermore, in this invention, the drug tape is mounted on a dispenser, so that it is necessary to have a definite tensile strength. Control for the tensile strength is therefore required in production, which is disadvantageous to efficiency in actual production. Still further, in the above-mentioned invention (C), the substance showing physiologically activity by the existence thereof in slight amounts (a drug: for example, 0.02 mg per unit, in the case of mestranol) is utilized. The drug is effectively used in such slight amounts, so that the solution or suspension of the drug is printed on, spread on, sprayed on, or injected into the sheet-shaped carrier. However, this is time-consuming and not economical. Then, with respect to one shown in FIG. 1 of the published specification, not only slights are provided, but also punching is performed with a punch, resulting in complication of the process.

An object of the invention is to economically provide a film preparation having no disadvantages observed in the above-mentioned known film preparations, that is to say, rapidly dissolved, simply produced and economically obtained.

DISCLOSURE OF THE INVENTION

The present inventors have variously studied for obtaining a film preparation having sufficient rapid solubility by a simple process by the addition of one ingredient. As a result, the present inventors have discovered that the use of a drug, an edible polymer and a monosaccharide, a sugar alcohol or an oligosaccharide in combination can solve the above-mentioned problems, thus completing the present invention.

That is to say, the present invention relates to (1) a rapidly soluble film preparation mainly comprising a drug, an edible polymer and a saccharide, (2) the rapidly soluble film preparation described in (1), in which the content of the drug is from 0.01 to 50% by weight, that of the edible polymer is from 20 to 90% by weight, and that of the saccharide is from 1 to 50% by weight, (3) the rapidly soluble film preparation described in (1), in which the drug is a compound enhanced in internal absorption by the conversion to a solid solution, (4) the rapidly soluble film preparation described in (3), in which the compound enhanced in internal absorption by the conversion to the solid solution is nilvadipine, (5) the rapidly soluble film preparation described in (1), in which the edible polymer is one selected from the group consisting of synthetic polymers, cellulose derivatives and natural polymers, (6) the rapidly soluble film preparation described in (1) or (5), in which the edible polymer is at least one selected from the group consisting of poly(vinylpyrrolidone), hydroxypropyl methyl cellulose, hydroxypropyl cellulose, methyl cellulose, hydroxyethyl cellulose and ethyl cellulose, (7) the rapidly soluble film preparation described in (1) or (2), in which the saccharide is one selected from the group consisting of monosaccharides, sugar alcohols and oligosaccharides, (8) the rapidly soluble film preparation described in (7), in which the oligosaccharide is starch syrup, (9) the rapidly soluble film preparation described in (8), in which the starch syrup is reducing maltose starch syrup, (10) the rapidly soluble film preparation described in (1), in which the drug is a compound which can be enhanced in internal absorption by the conversion to a solid solution, the edible polymer is one or more of poly(vinyl-pyrrolidone) and hydroxypropyl cellulose, and an additional edible polymer, and the saccharide is starch syrup, and (11) the rapidly soluble film preparation described in (10), in which the compound enhanced in internal absorption by the conversion to the solid solution is nilvadipine, the additional edible polymer is hydroxypropyl cellulose, and the starch syrup is reducing maltose starch syrup.

As apparent from the above, the film preparation of the invention is characterized in that it is rapidly dissolved in the oral cavity and can be taken without water, as a dosage form substitutive for a tablet.

The invention is described in detail below. The invention is the rapidly soluble film preparation in which the drug is allowed to be contained in a film base comprising the edible polymer such as poly (vinylpyrrolidone), hydroxypropyl methyl cellulose, hydroxypropyl cellulose, methyl cellulose, hydroxyethyl cellulose or ethyl cellulose, and the monosaccharide, the sugar alcohol or the oligosaccharide, and which is easily produced and has no conventional disadvantages as described above.

BEST MODE FOR CARRYING OUT THE INVENTION

Figure 1:
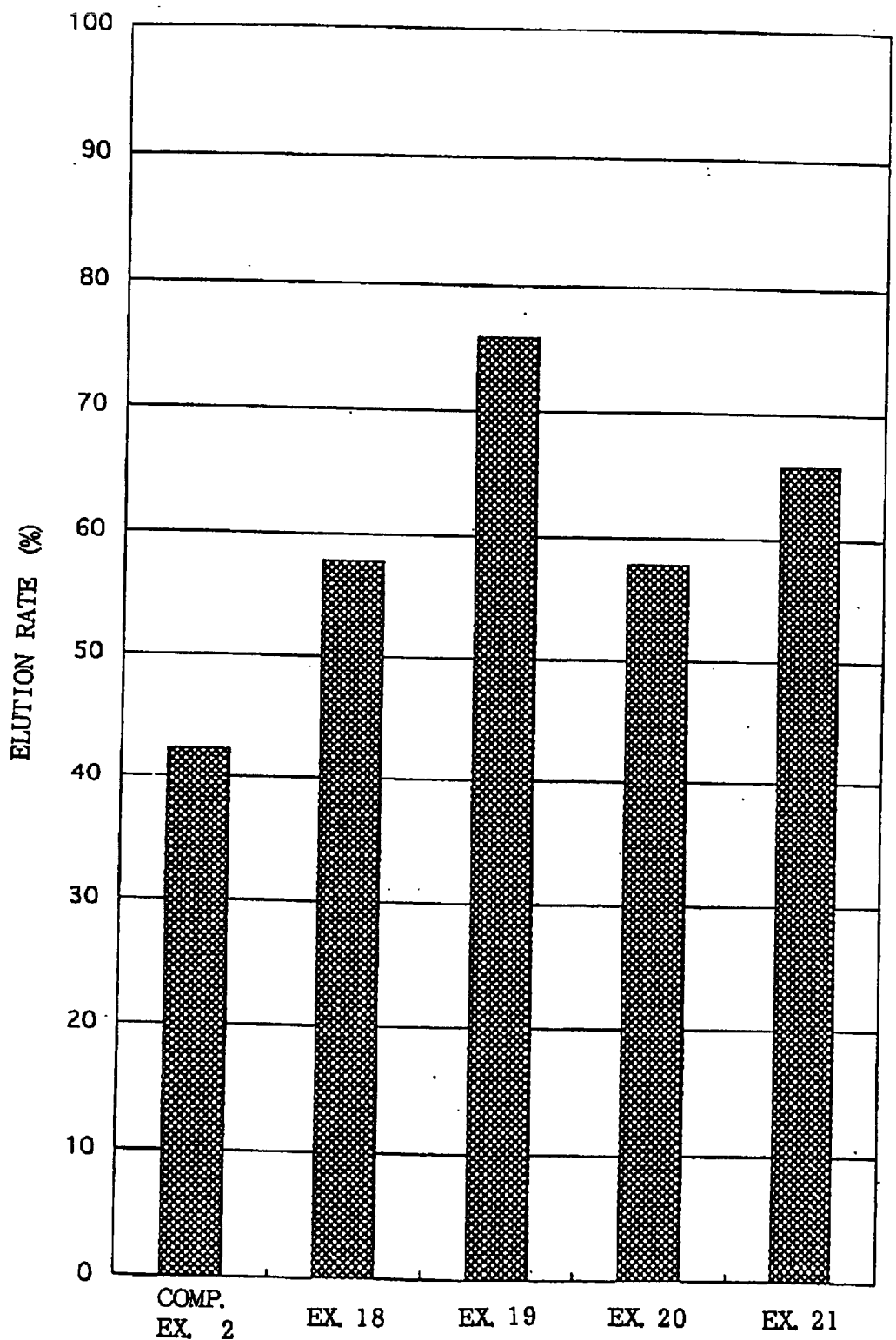
FIG. 1 is a graph showing the elution rate of a rapidly soluble film preparation of the invention.

The saccharides used in the invention include sugar alcohols such as erythritol, pentitol and hexitol, monosaccharides (aldose and ketose) and oligosaccharides. Specifically, the sugar alcohols include xylitol, mannitol, D-sorbitol and reducing maltose starch syrup, the monosaccharides include glucose and fructose, the oligosaccharides include maltose, lactose and sucrose, and the monosaccharide-oligosaccharides include starch syrup. Reducing maltose starch syrup is particularly preferred. The compounding amount of the saccharides in the film preparation of the present invention is from 1 to 50% by weight, and preferably from 5 to 50% by weight. Less than 1% results in the insufficient rate of dissolution, whereas exceeding 50% raises a problem with regard to the shape retaining property of products, although the rate of dissolution is increased. Many of the saccharides have sweet tastes, and this is advantageous for the film preparations soluble in the mouth. Further, many of them also act as plasticizers, like starch syrup. Accordingly, when they are used, it is not necessary to especially use plasticizers, of course, the plasticizers may be used as so desired. When sorbitol is used as the saccharide, sorbitol sometimes deposits as crystallites on film surfaces. However, the drug effect and the others are not affected at all.

There is no particular limitation on the edible polymer which is a component of the film base of the invention, as long as it has film forming ability and is edible. The edible polymers include synthetic polymers, for example, poly (vinylpyrrolidone) (hereinafter described as "PVP"), carboxyvinyl polymers (hereinafter described as "CVPs"), polyvinyl alcohol (hereinafter described as "PVA") and the like, cellulose derivatives, such as hydroxypropyl methyl cellulose (hereinafter described as "HPMC"), hydroxypropyl cellulose (hereinafter described as "HPC"), hydroxyethyl cellulose (hereinafter described as "HEC"), methyl cellulose (hereinafter described as "MC"), ethyl cellulose (hereinafter described as "EC") and the like, and polymers obtained from natural products, for example, sodium alginate, dextran, casein, pullulan and the like. Particularly preferred are PVP and HPC. These substances can be used either alone or as a combination of two or more of them.

The total compounding amount of the edible polymers in the film preparation is from 20 to 90% by weight, and preferably from 25 to 80% by weight in all.

For the rapidly soluble film preparations of the invention, aromatics, coloring matter, preservatives, antioxidants, stabilizing agents, surfactants, plasticizers and the like may be properly used as components of the film bases, as so desired, in addition to the above-mentioned substances.

There is no particular limitation on the drugs used in the invention, as long as they can be orally administered. Specific examples thereof include calcium antagonists such as nilvadipine and nicardipine, β2-stimulants such as procaterol hydrochloride and fenoterol hydrobromide, oral antidiabetic drugs such as glibenclamide, somniferous drugs such as brotizolam and triazolam, β-blockers such as arotinolol hydrochloride and carteolol hydrochloride, therapeutic drugs for the coronary vessels such as nicorandil, anesthetics such as dibucaine hydrochloride, nonsteroidal anti-inflammatory drugs such as diclofenac sodium and indomethacin, and sedatives such as diphenhydramine hydrochloride and scopolamine hydrobromide.

As the drugs used in the invention, ones having no bitter tastes are suitable. However, even ones having bitter tastes can be used in the invention by masking such as microcapsulation. The compounding amount of the drugs in the film preparation is usually from 1 to 50% by weight, although it varies depending on the properties of the drugs.

The rapidly soluble film preparations of the invention are produced, for example, by the following method.

Specified amounts of the edible polymer, saccharide and drug are dissolved in a solvent in which these substances are soluble, for example, ethanol, and the resulting solution is spread on a liner film and dried to obtain a film. The film is cut to a desired size, and hermetically packaged if necessary to provide a product. The dissolution of the drug can be accelerated by heating to about 50 to about 60° C. in preparing the solution. Further, when foams are developed in the solution in preparing it, standing overnight or vacuum deaeration is preferably conducted. There is no particular limitation on the solvent used in preparing the solution, as long as it dissolves the respective compounding components. Either a single solvent or a combined solvent may be used. Specifically, the solvents include ethanol, a mixture of ethanol and water, and the like.

In the invention, it has been found that when the specified edible polymers are used, some kinds of drugs are enhanced in internal absorption thereof. That is to say, for example, when the drug is nilvadipine, the use of poly-(vinylpyrrolidone) and/or hydroxypropyl methyl cellulose as the edible polymer(s) enhances the internal absorption. This is considered to be caused by the formation of a good solid solution by nilvadipine with these polymers. In this case, the film preparation can be produced by the use of only poly-(vinylpyrrolidone) and/or hydroxypropyl methyl cellulose as the edible polymer(s), but an additional edible polymer can provide a better film preparation. For example, in the case of nilvadipine, hydroxypropyl cellulose is suitably used.

Specific examples of the drugs forming the solid solutions with the edible polymers include nifedipine, phenytoin, chloramphenicol, griseofulvin, sulfamethizole and the like, as well as nilvadipine.

EXAMPLES

The invention is described below in detail with reference to examples. These examples are not to be construed as limiting the invention.

Example 1

To a suitable amount of ethanol, 4.0 parts by weight of nilvadipine, 76.0 parts by weight of HPC and 20.0 parts by weight of reducing maltose starch syrup were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Example 2

To a suitable amount of ethanol, 4.0 parts by weight of nilvadipine, 72.0 parts by weight of HPC, 4.0 parts by weight of PVP and 20.0 parts by weight of reducing maltose starch syrup were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Examples 3 to 6

According to formulations of Table 1, rapidly soluble film preparations were obtained in the same manner as with Example 2.

TABLE 1

| Name of Component | Examples | | | |
|---|---|---|---|---|
| | 3 | 4 | 5 | 6 |
| Nilvadipine | 4.0 | 4.0 | 4.0 | 4.0 |
| HPC | 64.0 | 56.0 | 51.0 | 46.0 |
| PVP | 12.0 | 20.0 | 20.0 | 20.0 |
| Reducing Maltose Starch Syrup | 20.0 | 20.0 | 25.0 | 30.0 |
| Total | 100.0 | 100.0 | 100.0 | 100.0 |

Example 7

To a suitable amount of ethanol, 4.0 parts by weight of nilvadipine, 72.0 parts by weight of HPC, 4.0 parts by weight of HPMC and 20.0 parts by weight of reducing maltose starch syrup were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Examples 8 to 14

According to formulations of Table 2, rapidly soluble film preparations were obtained in the same manner as with Example 7.

TABLE 2

| Name of Component | Examples | | | | | | |
|---|---|---|---|---|---|---|---|
| | 8 | 9 | 10 | 11 | 12 | 13 | 14 |
| Nilvadipine | 4.0 | 4.0 | 4.0 | 4.0 | 4.0 | 4.0 | 4.0 |
| HPC | 64.0 | 56.0 | 51.0 | 46.0 | 56.0 | 56.0 | 56.0 |
| HPMC | 12.0 | 20.0 | 20.0 | 20.0 | — | — | — |
| MC | — | — | — | — | 20.0 | — | — |
| EC | — | — | — | — | — | 20.0 | — |
| HEC | — | — | — | — | — | — | 20.0 |
| Reducing Maltose Starch Syrup | 20.0 | 20.0 | 25.0 | 30.0 | 20.0 | 20.0 | 20.0 |
| Total | 100.0 | 100.0 | 100.0 | 100.0 | 100.0 | 100.0 | 100.0 |

Example 15

To a suitable amount of ethanol, 20.0 parts by weight of nicardipine hydrochloride, 40.0 parts by weight of HPC, 20.0 parts by weight of PVP and 20.0 parts by weight of reducing maltose starch syrup were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Examples 16 to 21

According to formulations of Table 3, rapidly soluble film preparations were obtained in the same manner as with Example 15.

TABLE 3

| Name of Component | Examples | | | | | |
|---|---|---|---|---|---|---|
| | 16 | 17 | 18 | 19 | 20 | 21 |
| Fenoterol Hydro-Bromide | 5.0 | 4.0 | — | — | — | — |
| Indomethacin | — | — | 2.0 | 2.0 | 2.0 | 2.0 |
| HPC | 55.0 | 56.0 | 78.0 | 58.0 | 78.0 | 58.0 |
| PVP | 20.0 | 20.0 | — | — | — | 20.0 |
| Reducing Maltose Starch Syrup | 20.0 | — | 20.0 | 40.0 | — | 20.0 |
| D-Sorbitol | — | 20.0 | — | — | 20.0 | — |
| | 100.0 | 100.0 | 100.0 | 100.0 | 100.0 | 100.0 |

Examples 22 and 23

According to formulations of Table 4, rapidly soluble film preparations were obtained in the same manner as with Example 7.

TABLE 4

| Name of Component | Examples | |
|---|---|---|
| | 22 | 23* |
| Nilvadipine | 4.0 | 4.0 |
| PVP | 76.0 | 20.0 |
| EC | — | 56.0 |
| Reducing Maltose Starch Syrup | 20.0 | 20.0 |
| Total | 100.0 | 100.0 |

*Ethanol:purified water = 3:1

Example 24

To a suitable amount of an ethanol-purified water (2:1) mixture, 4.0 parts by weight of nilvadipine, 6.0 parts by weight of HPMC and 20.0 parts by weight of reducing maltose starch syrup were added and dissolved by stirring.

This was spread on a polyester separate film and dried to produce a film having a thickness of about 250 μm. The resulting film was cut to a square, 16 mm each side, thereby obtaining a film preparation rapidly soluble in the oral cavity.

Examples 25 to 28

According to formulations of Table 5, rapidly soluble film preparations were obtained in the same manner as with Example 24.

TABLE 5

| Name of Component | Examples | | | |
|---|---|---|---|---|
| | 25 | 26 | 27 | 28* |
| Nilvadipine | 4.0 | 4.0 | 4.0 | 4.0 |
| HPC | — | 56.0 | — | — |
| PVP | 20.0 | — | — | — |
| HPMC | — | 20.0 | 20.0 | 20.0 |
| MC | 56.0 | — | 56.0 | — |
| EC | — | — | — | 56.0 |
| Reducing Maltose Starch Syrup | 20.0 | 20.0 | 20.0 | 20.0 |
| Total | 100.0 | 100.0 | 100.0 | 100.0 |

*Ethanol:purified water = 3:1

Example 29

To a suitable amount of a mixture of ethanol-purified water (2:1), 4.0 parts by weight of nilvadipine, 38.0 parts by weight of PVP, 38.0 parts by weight of HPMC and 20.0 parts by weight of reducing maltose starch syrup were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Examples 30 to 32

According to formulations of Table 6, rapidly soluble film preparations were obtained in the same manner as with Example 29.

TABLE 6

| Name of Component | Examples | | |
|---|---|---|---|
| | 30 | 31 | 32* |
| Nilvadipine | 4.0 | 4.0 | 4.0 |
| HPC | 36.0 | — | — |
| PVP | 20.0 | 20.0 | 20.0 |
| HPMC | 20.0 | 20.0 | 20.0 |
| MC | — | 36.0 | — |
| EC | — | — | 36.0 |
| Reducing Maltose Starch Syrup | 20.0 | 20.0 | 20.0 |
| Total | 100.0 | 100.0 | 100.0 |

*Ethanol:purified water = 3:1

Comparative Example 1

To a suitable amount of ethanol, 4.0 parts by weight of nilvadipine, 76.0 parts by weight of HPC and 20.0 parts by weight of PVP were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

Comparative Example 2

To a suitable amount of ethanol, 2.0 parts by weight of indomethacin and 98.0 parts by weight of HPC were added and dissolved by stirring. This was spread on a polyester liner film and dried to produce a film having a thickness of about 250 μm. The resulting film was cut to a square, 16 mm each side, thereby obtaining a film preparation rapidly soluble in the oral cavity.

(Elution Test)
Test Method

In a 100-ml tall beaker, 100 ml of purified water is placed, and stirred (100 rpm) with a stirrer. One piece of sample (16 mm×16 mm) is placed in a cylindrical stainless steel basket, and put under the water in the beaker. Then, the basket is fixed. After a definite period of time from initiation of the test, 500 μl was sampled, and determined with the HPLC. Results are shown in FIG. 1.

Industrial Applicability

The film preparations of the invention are very easily produced, have high rapid solubility, are extremely high in practical use, and are suitable for using as film preparations for oral administration.

What is claimed is:

1. A water soluble film preparation for oral administration comprising nilvadipine, an edible polymer which is one or more of poly(vinylpyrrolidone) and hydroxypropyl cellulose, and an oligosaccharide which is reducing maltose starch syrup, and wherein the film preparation further comprises an additional edible polymer selected from the group consisting of poly(vinylpyrrolidone), hydroxyprpyl methyl cellulose, hydroxypropyl cellulose, methyl cellulose, hydroxyethyl cellulose and ethyl cellulose.

* * * * *